United States Patent [19]

Sneider

[11] 4,318,403
[45] Mar. 9, 1982

[54] FOLDABLE NOZZLE SYRINGE

[76] Inventor: Vincent R. Sneider, 3422 Hallcrest Dr., NE., Atlanta, Ga. 30319

[21] Appl. No.: 172,081

[22] Filed: Jul. 24, 1980

[51] Int. Cl.³ .............................................. A61M 1/00
[52] U.S. Cl. .................................... 128/232; 128/239; 222/538
[58] Field of Search ............... 128/232, 224, 227, 225, 128/213, 251, 248, 239; 222/538, 527; 220/90.2, 90.4

[56] References Cited

U.S. PATENT DOCUMENTS

| | | | |
|---|---|---|---|
| 2,516,728 | 7/1950 | Smith | 222/538 |
| 2,568,915 | 9/1951 | Friedman | 128/232 X |
| 3,329,316 | 7/1967 | Lowe | 222/538 |
| 3,401,695 | 9/1968 | Rosenberg et al. | 128/232 |
| 3,476,111 | 11/1969 | Matheson | 128/227 |
| 3,802,434 | 4/1974 | Brooks | 128/232 |
| 4,066,080 | 1/1978 | Sneider | 128/232 |
| 4,112,942 | 9/1978 | Scaife | 128/225 |

Primary Examiner—John D. Yasko
Attorney, Agent, or Firm—Ralph R. Roberts

[57] ABSTRACT

A syringe is disclosed for vaginal douche, swab, or like applications. A flexible fluid container has an elongated tubular discharge nozzle molded integrally therewith as an extension of one end of the container, and at least the juncture of the nozzle and the container is flexible to facilitate bending and folding of the nozzle to a position alongside the container. An elongated slot is formed on the side of the container for receiving the nozzle when in its folded position substantially within the outer confines of the container. Detent protrusions along opposite edges of the slot releasably retain the nozzle in its folded position within the slot. The entire foldable nozzle syringe is formed as an integral molded and prefilled construction, and an integral frangible cap is provided on the distal end of the nozzle, the latter being threaded for attachable association with a douche, swab or other attachment.

18 Claims, 5 Drawing Figures

U.S. Patent  Mar. 9, 1982  4,318,403
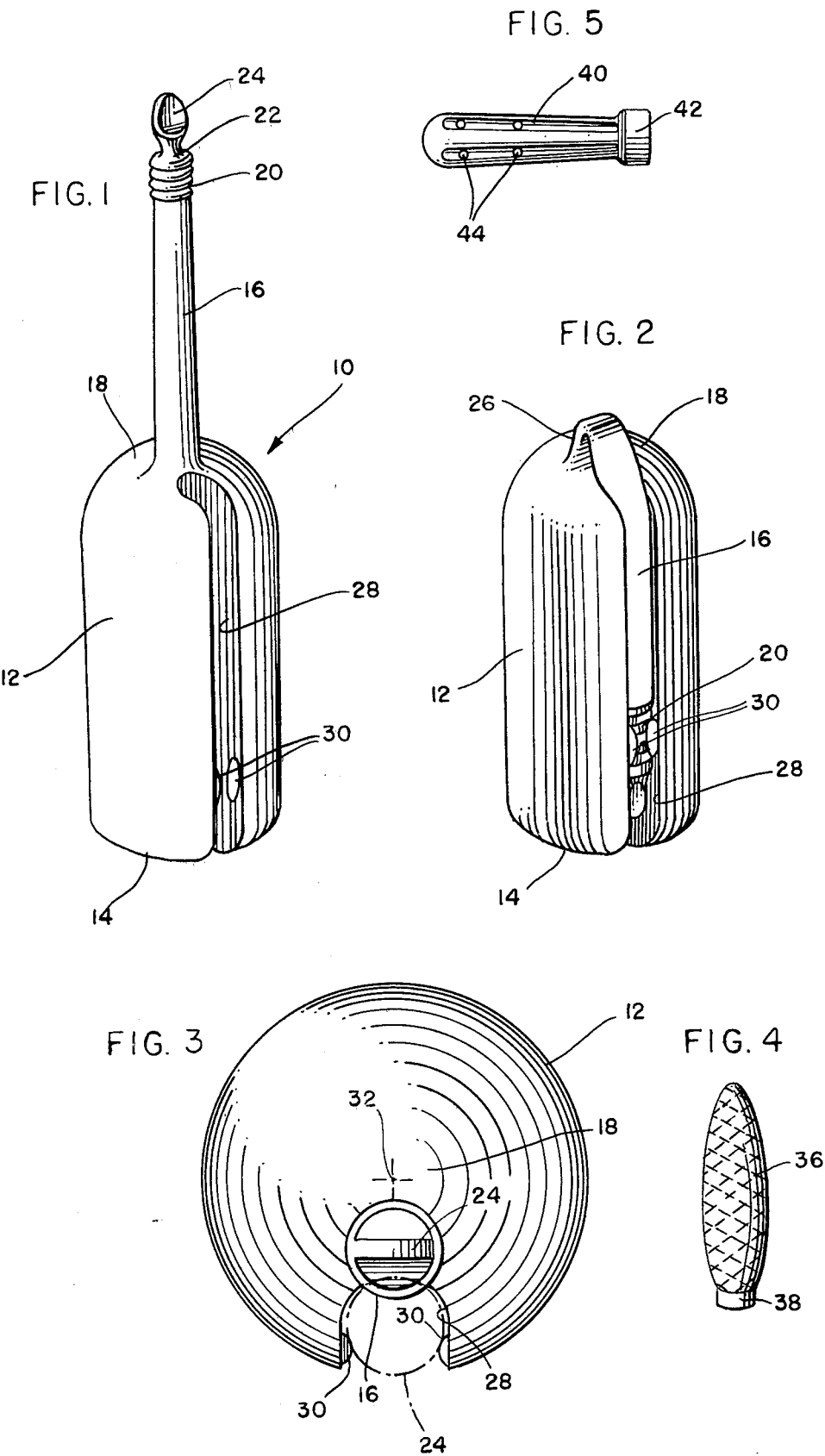

FOLDABLE NOZZLE SYRINGE

BACKGROUND OF THE INVENTION

This invention relates to syringes and particularly to syringes which have fluid discharge nozzles for use as vaginal douches, swabs, or the like.

It has become increasingly important to provide vaginal applicators which are economical to manufacture and which utilize inexpensive materials so that the applicators may be disposable, that is employed for a single use and then discarded. It also is important to provide a vaginal applicator which is inherently hygienic. To this end, such applicators have become increasingly popular which are manufactured and prefilled at a manufacturing plant under sanitary conditions, then sealed until ready for use. The containers of such applicators can be prefilled with medicaments or simply with cleansing and rinsing solutions.

One of the problems in providing economical and inexpensive disposable vaginal applicators is that separate fluid discharge nozzles are fabricated and packaged separately with a flexible container, and the nozzles are attached to the container after purchase, prior to application by the user. Some examples of such vaginal applicators are those presently on the market are those under the names of "Feminique" TM of Ennis Laboratories, Edison, N.J.; "Massengill" TM of Beecham Products, Pittsburgh, Pa.; and "Summer's Eve" TM of C. B. Fleet Co., Inc., Lynchburg, Va. With these and other similar products presently on the market, separate elongated fluid discharge nozzles are packaged separately with the prefilled containers.

With such vaginal applicators as described above, not only is the cost of manufacture substantially increased for a preferably inexpensive product, but the increased sized of the packaging therefor tends to decrease the amount of display-shelf area alotted by the retailer to such an important product.

The present invention is designed to provide a new and improved syringe for vaginal applicators which solves these and other problems.

SUMMARY OF THE INVENTION

An object, therefore, of the present invention is to provide a new and improved inexpensive, easily manufactured syringe for vaginal applicators.

Another object of the present invention is to provide a syringe of the charactered described which has an integral, novel foldable fluid discharge nozzle in a prefilled disposable syringe for vaginal douche, swab, or like applications.

In the exemplary embodiment of the invention, the syringe includes a flexible molded plastic fluid container. An elongated tubular discharge nozzle is molded integral with and as an extension of one end of the flexible container. At least the juncture between the nozzle and the container also is flexible to facilitate bending and folding of the nozzle alongside the container. An elongated slot is formed on the side of the container for receiving the nozzle when in its folded position. The slot has a depth substantially equal to the diameter of the tubular nozzle so that the nozzle can be received in the slot substantially completely within the outer confines of the container. In this manner, the entire packaging dimensions for the syringe is considerably reduced. In addition, the integral nozzle is considerably less expensive and more easy to manufacture than providing separately made and packaged nozzle attachments as are heretofore available.

In the invention disclosed and described herein, the nozzle is disposed at the one end of the container immediately adjacent an open end of the elongated slot, with the center of the tubular nozzle disposed approximately one-half the diameter thereof from the opened end of the slot so that the nozzle can be folded directly into the slot.

An important feature of the invention is the provision of means for releasably retaining the nozzle in its folded position within the slot. As shown herein, this retaining means comprises a pair of detent protrusions along opposite outer edges of the slot and behind which the nozzle can be snapped into the slot.

Another feature of the invention is the provision of an integral frangible cap on the distal end of the nozzle so that the syringe can be formed as an integral molded and prefilled construction. The distal end of the nozzle also is threaded for receiving a relatively small douche, swab, or like applicator attachment.

Other objects, features and advantages of the invention will be apparent from the following detailed description taken in connection with the accompanying drawings.

DESCRIPTION OF THE DRAWINGS

FIG. 1 is a perspective view of the foldable nozzle syringe of the present invention, with the nozzle thereof extending from the container in normal use condition;

FIG. 2 is a perspective view of the syringe of FIG. 1, with the nozzle in its fully folded, stored position;

FIG. 3 is a top plan view, on an enlarged scale, of the syringe of FIG. 1, illustrating the offset disposition of the nozzle;

FIG. 4 is an elevational view of a swab attachment for use with the syringe of FIG. 1; and FIG. 5 is an elevational view of a douche attachment for use with the syringe of FIG. 1.

DETAILED DESCRIPTION OF THE INVENTION

Referring to the drawings in greater detail, and first to FIG. 1, a syringe, generally designated 10, in accordance with the present invention is shown, particularly for vaginal douche, swab, or like applications. The syringe includes a rounded molded flexible container 12 having a generally flat bottom 14 thereof for supporting the syringe on an appropriate subjacent support surface. The container preferably is fabricated of plastic or like material so that the container can be collapsed by a user to discharge liquid therefrom.

A tubular fluid discharge nozzle 16 is molded integral with and as an extension of one end 18 of the flexible container 12. The nozzle has a threaded portion 20 on the distal end thereof for attachable association with a douche, swab or like attachment, described hereinafter. Like the container 12, nozzle 16 is molded of plastic material and is closed at its distal end 22 by a frangible cap 24 which is shown in the form of a finger graspable tab. The tab can be twisted by a user to fracture cap 22 so that fluid can be discharged from container 12 through nozzle 16. In this manner, the entire syringe assembly 10 is formed as an integral molded and prefilled construction and can be disposable after a single use.

Referring to FIG. 2, an important feature of the invention is that at least the juncture 26 between nozzle 16 and container 12 is sufficiently flexible so that the nozzle can be bent and folded to a position alongside the container. Preferably, juncture 26 is sufficiently flexible to permit said folding, but the juncture is sufficiently self substaining so as to maintain the nozzle in an upright or extended position as shown in FIG. 1 for proper use applications.

As seen in both FIGS. 1 and 2, recess means in the form of an elongated slot 28 is formed on the side of container 12. The slot has a depth substantially equal to the diameter of the tubular nozzle so that the nozzle can be received when in its folded position substantially completely within the outer confines of the container. It readily can be seen in FIG. 2 that, with this construction, the overall dimensions of the syringe assembly is greatly reduced from prior assemblies which utilize separate complete nozzle attachements. Obviously, packaging and shelf storage space for the syringe assembly is reduced.

Means also is provided for releasably retaining nozzle 16 in its folded or stored position within slot 28. More particularly, a pair of detent protrusions 30 are formed on opposite facing outer edges of slot 28. The detent protrusions enable the nozzle to be snapped into and retained within slot 20 in a stored condition. As shown herein, the detent protrusions are disposed in an area so as to be engageable with the threaded portion 20 of the nozzle, since the threaded portion normally would have more rigidity than the remainder of the nozzle.

Referring to FIG. 3, it can be seen that nozzle 16 is disposed on the end 18 of container 12 offset relative to the center 32 of the container. This disposition of the nozzle facilitates bending the nozzle alongside the container. In particular, in the exemplary embodiment of the invention, nozzle 16 is disposed immediately adjacent the upper open end of slot 28, with the center of the nozzle disposed approximately one-half the diameter thereof from the opened end of the slot so that the nozzle can be folded directly into the slot.

Referring to FIG. 4, a swab attachment, generally designated 36, is shown with an internally threaded portion 38 for attachment to the threaded portion 20 of nozzle 16. The swab may be fabricated of various suitable cotton or tampon materials.

Referring to FIG. 5, a douche attachment, generally designated 40, is shown with an internally threaded portion 42 for attachment with the threaded portion 20 of nozzle 16. As is known, the douche attachment is generally hollow and has apertures 44 for the discharge of fluid therethrough for douching purposes.

As can be seen from the swab and douche attachments shown in FIGS. 4 and 5, respectively, the attachments are greatly reduced relative to the overall nozzle attachments of syringe assemblies heretofore available. In fact, such attachments can be fabricated so as not to exceed the cross dimensions of container 12. In this manner, the attachments can be packaged on top of the syringe 10 in an appropriate carton and not add to the overall packaging dimensions of the product. This is quite important in dealing with such desirably inexpensive and disposable applicators.

It will be understood that the invention may be embodied in other specific forms without departing from the spirit or central characteristics thereof. The present examples and embodiments, therefore, are to be considered in all respects as illustrative and not restrictive, and the invention is not to be limited to the details given herein.

I claim:

1. A syringe for vaginal douche, swab or like applications, including:
   (a) a flexible container having an outlet at one end thereof;
   (b) a discharge nozzle attached at said outlet of the flexible container with the nozzle having an elongated portion disposed to be folded near its connection to be positioned alongside the flexible container;
   (c) a longitudinal groove formed in and at the side of said flexible container and open outwardly thereof so that when the flexible container is filled said longitudinal groove in the side of the flexible container is shaped to receive and releasably retain the discharge nozzle within said groove.

2. The syringe of claim 1 wherein said longitudinal groove includes at least one detent protrusion extending inwardly at an outer edge of said longitudinal groove.

3. The syringe of claim 2, including a pair of said detent protrusions facing each other on opposite edges of said longitudinal groove.

4. The syringe of claim 1 wherein said discharge nozzle is elongated for receiving the discharge nozzle.

5. The syringe of claim 4 wherein said nozzle is formed integral with and as an extension of said container.

6. The syringe of claim 5 wherein said syringe is formed as an integral molded and prefilled construction, and including an integral frangible cap on the distal end of said discharge nozzle.

7. The syringe of claim 1 wherein said discharge nozzle is molded integral with and as an extension of said flexible container, and wherein at least the juncture of said discharge nozzle and said flexible container is flexible to facilitate bending of the discharge nozzle alongside the flexible container into said longitudinal groove.

8. The syringe of claim 7 wherein said discharge nozzle is disposed at one end of said container offset relative to the center of said one end to facilitate bending the discharge nozzle alongside the flexible container.

9. The syringe of claim 1 wherein said discharge nozzle is generally tubular and said longitudinal groove having a depth substantially equal to the diameter of said discharge nozzle so that the discharge nozzle can be received and retained in said longitudinal groove and substantially completely within the outer confines of the flexible container.

10. The syringe of claim 9 wherein said discharge nozzle is disposed at one end of said flexible container immediately adjacent an open end of said longitudinal groove and with the center of the tubular nozzle disposed approximately one-half the diameter thereof from said open end of the longitudinal groove so that the discharge nozzle can be folded directly into said longitudinal groove.

11. The syringe of claim 1, including means on the distal end of said discharge nozzle for attachable association with a douche, swab or other attachment.

12. A syringe for vaginal douche, swab or like applications, including:
   (a) a flexible container having an outlet at one end thereof;

(b) an elongated tubular discharge nozzle molded integral with and as an extension of said flexible container, and at least the juncture of said nozzle and said container being flexible to facilitate bending and folding of the discharge nozzle to a position alongside the flexible container; and (c) an elongated groove in the side of the flexible container and when the flexible container is filled said longitudinal groove in the side of the flexible container is shaped to receive and releasably retain the discharge nozzle when in said folded condition, said groove having a depth substantially equal to the diameter of said discharge nozzle so that the discharge nozzle can be received in said flexible container substantially completely within the outer confines of the container.

13. The syringe of claim 12 wherein said discharge nozzle is disposed at one end of said flexible container immediately adjacent an open end of said groove and with the center of the tubular nozzle disposed approximately one-half the diameter thereof from said open end of the groove so that the discharge nozzle can be folded directly into said longitudinal groove.

14. The syringe of claim 12 wherein the longitudinal groove is formed with a pair of detent protrusions opposite each other along opposite edges of said longitudinal groove.

15. The syringe of claim 12 wherein said syringe is formed as an integral molded and prefilled construction, and including an integral frangible cap on the distal end of said discharge nozzle.

16. The syringe of claim 12, including means on the distal end of said discharge nozzle for attachable association with a douche, swab or other attachment.

17. The syringe of claim 16 including, in combination, a swab attachment for securing to the distal end of said discharge nozzle.

18. The syringe of claim 16 including, in combination, a douche attachment for securing to the distal end of said discharge nozzle.

* * * * *